US008765155B2

(12) United States Patent
Mello et al.

(10) Patent No.: US 8,765,155 B2
(45) Date of Patent: Jul. 1, 2014

(54) ORAL CARE STRIP OR TAPE AND METHODS OF USE AND MANUFACTURE THEREOF

(75) Inventors: Sarita V. Mello, Somerset, NJ (US); Evangelia S. Arvanitidou, Princeton, NJ (US)

(73) Assignee: Colgate-Palmolive Company, New York, NY (US)

( * ) Notice: Subject to any disclaimer, the term of this patent is extended or adjusted under 35 U.S.C. 154(b) by 1456 days.

(21) Appl. No.: 11/847,935

(22) Filed: Aug. 30, 2007

(65) Prior Publication Data

US 2009/0060958 A1 Mar. 5, 2009

(51) Int. Cl.
*A61K 8/02* (2006.01)
*A61K 8/21* (2006.01)
*A61K 8/24* (2006.01)
*A61K 8/97* (2006.01)
*A61Q 11/00* (2006.01)

(52) U.S. Cl.
USPC .................. 424/401; 424/52; 424/57; 424/58

(58) Field of Classification Search
USPC .......................................................... 424/53
See application file for complete search history.

(56) References Cited

U.S. PATENT DOCUMENTS

| 3,535,421 A | 10/1970 | Briner et al. |
| 3,538,230 A | 11/1970 | Pader et al. |
| 3,678,154 A | 7/1972 | Widder et al. |
| 3,696,191 A | 10/1972 | Weeks |
| 3,862,307 A | 1/1975 | Di Giulio |
| 3,937,807 A | 2/1976 | Haefele |
| 3,959,458 A | 5/1976 | Agricola et al. |
| 3,991,177 A | 11/1976 | Vidra et al. |
| 4,051,234 A | 9/1977 | Gieske et al. |
| 4,058,595 A | 11/1977 | Colodney |
| 4,154,815 A | 5/1979 | Pader |
| 4,340,583 A | 7/1982 | Wason |
| 4,355,022 A | 10/1982 | Rabussay |
| 4,649,044 A * | 3/1987 | Gomi et al. ..................... 424/49 |
| 4,842,847 A | 6/1989 | Amjad |
| 4,866,161 A | 9/1989 | Sikes et al. |
| 4,885,155 A | 12/1989 | Parran, Jr. et al. |
| 4,992,420 A | 2/1991 | Neeser |

(Continued)

FOREIGN PATENT DOCUMENTS

| CA | 2557718 | 10/2005 |
| CN | 1082864 | 3/1994 |

(Continued)

OTHER PUBLICATIONS

NICNAS, Existing Chemicals Information Sheet, Sodium Lauryl Sulfate, 2003, pp. 1-6.*

(Continued)

*Primary Examiner* — Brian Gulledge
*Assistant Examiner* — Celeste A Roney
(74) *Attorney, Agent, or Firm* — Howard C. Lee

(57) ABSTRACT

This invention relates to oral care composition, methods of use and methods of manufacture thereof in the form of a toothtape that can be used to brush or clean teeth and the oral cavity. Particularly, the invention relates to a non-traditional dentifrice that comes in the form of a tape that can, for example, adhere to the oral cavity and particularly the teeth and be dispensed for single use.

14 Claims, 1 Drawing Sheet

(56) References Cited

U.S. PATENT DOCUMENTS

| | | | |
|---|---|---|---|
| 4,998,978 A | 3/1991 | Varum | |
| 5,000,939 A | 3/1991 | Dring et al. | |
| 5,004,597 A | 4/1991 | Majeti et al. | |
| 5,008,106 A * | 4/1991 | Merianos et al. | 424/78.06 |
| 5,354,551 A | 10/1994 | Schmidt | |
| 5,961,958 A | 10/1999 | Homola et al. | |
| 6,153,222 A | 11/2000 | Becher | |
| 6,177,096 B1 | 1/2001 | Zerbe | |
| 6,545,077 B2 | 4/2003 | Hill et al. | |
| 6,609,527 B2 | 8/2003 | Brown | |
| 6,682,722 B2 | 1/2004 | Majeti et al. | |
| 2002/0127190 A1 | 9/2002 | Zerbe | |
| 2003/0228264 A1* | 12/2003 | Perna | 424/53 |
| 2004/0219112 A1* | 11/2004 | Oniki et al. | 424/53 |
| 2007/0140985 A1* | 6/2007 | Boyd et al. | 424/49 |

FOREIGN PATENT DOCUMENTS

| | | |
|---|---|---|
| DE | 202007006651 U1 | 7/2007 |
| EP | 0702948 | 3/1996 |
| EP | 0 867 174 A | 9/1998 |
| JP | 3043804 | 5/2000 |
| JP | 2004-010576 | 1/2004 |
| JP | 2005-247876 | 9/2005 |
| JP | 2007-169181 | 7/2007 |
| JP | 2007-197540 | 8/2007 |
| RU | 2190982 | 10/2002 |
| RU | 2279864 | 7/2006 |
| WO | WO 03/030851 | 4/2003 |
| WO | 2006108432 A1 | 10/2006 |
| WO | WO 2007083253 | 7/2007 |

OTHER PUBLICATIONS

International Search Report Dated Nov. 19, 2008.
International Preliminary Report on Patentability from the International Bureau for International Application No. PCT/US2008/070123 mailed Mar. 11, 2010.

* cited by examiner

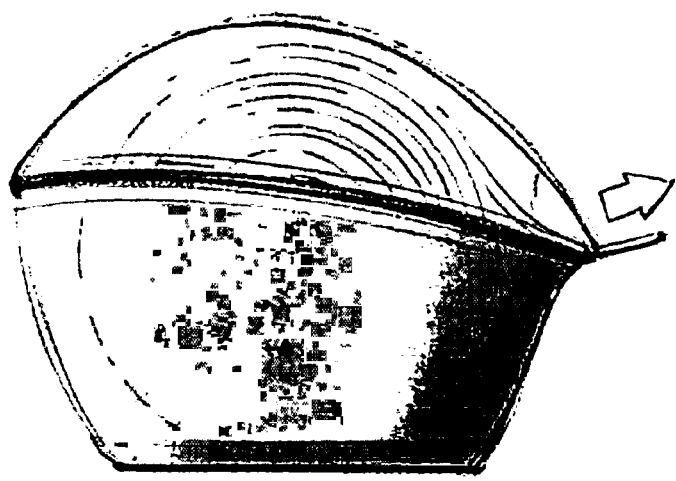
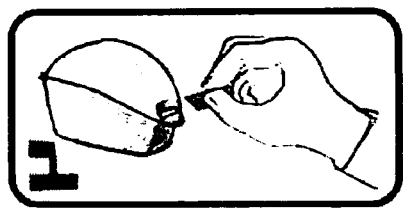
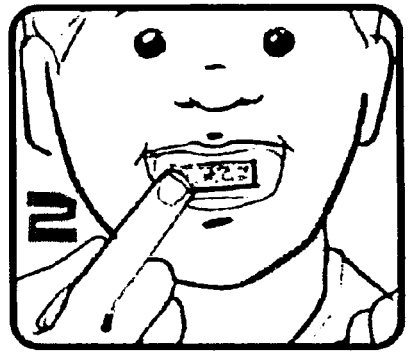
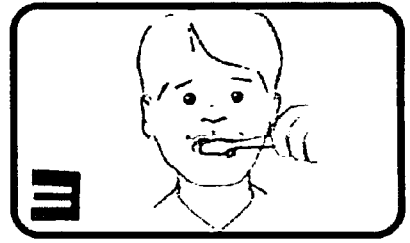

ORAL CARE STRIP OR TAPE AND METHODS OF USE AND MANUFACTURE THEREOF

BACKGROUND OF THE INVENTION

The formation of dental plaque is a source of gingival and periodontal disease and subsequent tooth loss. Dental plaque is a mixed matrix of bacteria, epithelial cells, leukocytes, macrophages and other oral exudate. Bacteria comprise approximately three-quarters of the plaque matrix. Any given sample of dental plaque could contain as many as 400 different varieties of microorganisms. This mix includes both aerobic and anaerobic bacteria, fungi and protozoa. Viruses have also been found in samples of dental plaque.

This matrix of organisms and oral exudate continues expanding and coalesces with other plaque growths situated nearby. The bacteria synthesize levans and glucans from sucrose found in the oral cavity providing energy for the microorganisms. These glucans, levans and microorganisms form an adhesive skeleton for the continued proliferation of plaque.

Calculus is a yellow or white mineralized deposit of bacterial plaque. Inorganic in nature, calculus consists primarily of calcium and magnesium phosphate and calcium carbonate. Calculus forms in layers as does plaque and is simply the mineralization of plaque's layered bacteria. Calculus is formed when plaque's protein-carbohydrate matrix accumulates calcium followed by the precipitation and mineralization of crystalline calcium phosphate. Once mineralized calculus is formed, another layer of bacteria adheres to the surface forming yet another layer of plaque winch is subsequently mineralized into calculus.

The failure to retard or stop the proliferation of plaque is detrimental to oral health. Plaque formation leads to dental caries, gingival inflammation, periodontal disease and ultimately tooth loss. The present inventors recognize these problems and have developed a composition suitable for combating oral disease preventing tooth loss, and leading to general oral well-being.

While the prior art discloses the use of various oral compositions for combating plaque, there is still a need for additional formulations, which provide greater availability, improved performance in combating oral disease along with increased user acceptance. The present inventors have discovered the use of traditional dentifrice ingredients in a base in order to create a non-traditional, portable and consumer desirable toothtape.

BRIEF SUMMARY OF THE INVENTION

The present invention encompasses oral care products and methods of using the same that are effective in arresting the accumulation of plaque and preventing gingivitis. The invention also encompasses an oral product and methods that by reducing plaque will abate subsequent calculus formation. The invention also encompasses compositions and methods to provide consumers with a product that will clean the oral cavity and provide improved methods of promoting vitality of the oral cavity.

In one embodiment, the invention encompasses an oral care product in the form of a tape or strip that can be utilized to clean the oral cavity.

Another embodiment of the invention encompasses an oral care tape or strip capable of adhering to the surface of the oral cavity including an amount of oral care composition, wherein said oral care composition is capable of cleaning the teeth and/or oral cavity.

Another embodiment of the invention encompasses a tape or strip, which includes at least one abrasive, at least one surfactant, at least one foaming agent, and wherein the tape or strip can adhere to the surface of the oral cavity and is capable of cleaning the teeth and/or oral cavity, particularly with brushing.

Another embodiment of the invention encompasses a composition including an oral care tape or strip including at least one abrasive, at least one surfactant, and at least one fluoride source, wherein the oral care tape or strip can adhere to the surface of the oral cavity and is capable of cleaning the teeth and/or oral cavity.

Another embodiment of the invention encompasses a method of cleaning the oral cavity by adhering an oral care tape or strip to the surface of the oral cavity, for example, the teeth wherein the tape or strip includes at least one abrasive, at least one surfactant, at least one foaming agent and at least one fluoride source, wherein after the tape or strip is adhered to the surface of the oral cavity the oral cavity is brushed to clean the oral cavity.

Another embodiment of the invention encompasses a kit including an oral brushing tape or strip, which tape or strip is capable of adhering to the surface of the oral cavity, wherein the oral brushing strip includes at least one abrasive at least one surfactant, at least one fluoride source and at least one foaming agent, wherein the oral brushing strip can adhere to the surface of the oral cavity and is capable of cleaning the teeth and/or oral cavity, and wherein the kit contains the tape or strip is predetermined lengths for single use.

To achieve the foregoing and other embodiments and in accordance with the purpose of the present invention, as embodied and broadly described herein the oral tape or strip of this invention includes at least one abrasive, at least one surfactant, at least one fluoride source, and one or more optional components including vitamins, polymers, enzymes, humectants, preservatives and combinations thereof.

DETAILED DESCRIPTION OF THE DRAWINGS

FIG. 1 shows an alternative dispenser for the toothtape of the invention, and its use.

DETAILED DESCRIPTION OF THE INVENTION

As used throughout, ranges are used as a shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

The invention encompasses an oral tape or strip capable of adhering to the surface of the oral cavity including an amount of oral care composition, wherein said oral care composition. As used herein and unless otherwise indicated, the term "oral care composition" refers to a composition containing the oral care ingredients described herein. In certain embodiments, the oral tape or strip includes at least one abrasive. In another embodiment, the oral tape or strip includes at least one fluoride ion source. In another embodiment, the oral tape or strip includes at least one agent to increase the amount of foam generated upon use. In another embodiment, the oral tape or strip includes at least one flavoring agent.

In certain embodiments, the oral tape or strip is contained in a package in precut segments for single use, which can be adhered to the oral cavity, for example, the teeth, and a source of agitation (such as a conventional toothbrush) is applied to break up and/or aid in the dissolution of the toothtape in the oral cavity. Alternatively, the toothtape of the invention may be spooled and dispensed by cutting or trimming a portion of desired length from the spool. The length of the tape may contain perforations or detachable areas at increments so as to allow for easy separation from the length of toothtape.

In another embodiment, the oral tape or strip further includes at least one vitamin, at least one polymer, at least one fluoride source, at least one enzyme, at least one humectant, and/or at least one preservative and combinations thereof.

In certain embodiments, the abrasive includes, but is not limited to, abrasive silica, sodium metaphosphlate, potassium metaphosphate, tricalcium phosphate, dihydrated dicalcium phosphate, aluminum silicate, calcined alumina, bentonite or other siliceous materials, or combinations thereof.

In certain embodiments, the fluoride source includes, but is not limited to, sodium fluoride, potassium fluoride, sodium fluorosilicate, sodium monfluorophosphate (MFP), ammonium fluorosilicate, stannous fluoride and stannous chloride.

In certain embodiments, the agent to increase the amount of foam includes, but is not limited to, sodium alginate and polyoxyethylene.

In certain embodiments, the flavoring agent is one member chosen from oil of wintergreen, oil of peppermint, oil of spearmint, oil of sassafras, oil of clove, aspartame, acesulfame, saccharin, dextrose, levulose and sodium cyclamate and combinations thereof.

In certain embodiments, the abrasive is present in an amount of about 1 to 20 wt. %. In certain embodiments, the fluoride source is present in an amount of about 0.01 to 5 wt. %. In certain embodiments, the agent to increase the amount of foam is present in an amount of about 1 to 90 wt. %. In certain embodiments, the flavoring agent in an amount of about 0.01 to 5 wt. %. In certain embodiments, the tape or strip further includes at least one humectant in an amount of about 0.01 to 5 wt. %.

Another embodiment encompasses a composition including an oral brushing tape or strip capable of adhering to the surface of the oral cavity for single use, wherein the oral brushing strip has a surface area of about 20 to 1000 $mm^2$.

The oral care strip or tape compositions may include one or more abrasives, which may be used in the practice of the invention including, but are not limited to, silica abrasives such as precipitated silicas having a mean particle size of up to about 20 microns, such as Zeodent 115®, marketed by J. M. Huber. Useful abrasives also include sodium metaphosphate, potassium metaphosphate, tricalcium phosphate, dehydrated dicalcium phosphate, aluminum silicate, calcined alumina, bentonite or other siliceous materials, or combinations thereof. The silica abrasive polishing materials useful herein, as well as the other abrasives, generally have an average particle size ranging between about 0.1 and 30 microns, from between 5 and 15 microns. The silica abrasives can be from precipitated silica or silica gels, such as the silica xerogels described in U.S. Pat. No. 3,538,230, to Pader et al. and U.S. Pat. No. 3,862,307, to Digiulio, both incorporated herein by reference. Particular silica xerogels are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 115 and 119. These silica abrasives are described in U.S. Pat. No. 4,340,583, to Wason, incorporated herein by reference.

In certain embodiments, abrasive materials useful in the practice of the oral care strips or tape compositions in accordance faith the invention include silica gels and precipitated amorphous silica having an oil absorption value of about less than 100 cc/100 g silica and in the range of from about 45 cc/100 g to 70 cc/100 g silica. Oil absorption values are measured using the ASTA Rub-Out Method D281. In certain embodiments, the silicas are colloidal particles having an average particle size ranging from about 3 microns to 12 microns, and about 5 to 10 microns.

Low oil absorption silica abrasives particularly useful in the practice of the invention are marketed under the trade designation Sylodent XWA® by Davison Chemical Division of W.R. Grace & Co., Baltimore, Md. 21203. Sylodent 650 XWA®, a silica hydrogel composed of particles of colloidal silica having a water content of 29% by weight averaging from about 7 to 10 microns in diameter, and an oil absorption of less than 70 cc/100 g of silica is an example of a low oil absorption silica abrasive useful in the practice of the present invention. The abrasive is present in the oral care strip or tape composition of the present invention at a concentration of about 1 to 40% by weight, in other embodiment about 5 to 30% by weight, and in another embodiment about 10 to 20% by weight. The dosage of abrasive in the individual strip or tape (i.e., a single dose) is about 0.01 to 0.4% by weight, 0.05 to 0.3% by weight, and in another embodiment about 0.1 to 0.2% by weight.

The oral care strip or tape compositions may further include one or more fluoride ion sources. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran. Jr. et al. and U.S. Pat. No. 3,678,154, to Widder et al., incorporated herein by reference.

Representative fluoride ion sources include, but are not limited to, stannous fluoride, sodium fluoride, potassium fluoride, sodium monofluorophosphate, sodium fluorosilicate, sodium monfluorophosphate (MFP), ammonium fluorosilicate, as well as tin fluorides, such as stannous fluoride and stannous chloride, and combinations thereof. Certain particular embodiments include stannous fluoride or sodium fluoride as well as mixtures thereof.

In certain embodiments, the oral care strip or tape oral composition of the invention may also contain a source of fluoride ions or fluorine-providing ingredient in amounts sufficient to supply about 25 ppm to 5,000 ppm of fluoride ions.

Fluoride ion sources may be added to the compositions of the invention at a level of from about 0.01% to 3.0% in one embodiment or from about 0.03% to 1.0%, by weight of the composition in another embodiment. The dosage of the individual strip or tape (i.e., a single dose) is about 0.0001 to 0.003% by weight, 0.0005 to 0.003% by weight, and in another embodiment about 0.001 to 0.02% by weight.

The oral care strips or tape compositions of the invention also may include an agent to increase the amount of foam that is produced when the strip or tape adhered to the oral cavity is brushed or otherwise agitated.

Illustrative examples of agents that increase the amount of foam include, but are not limited to polyoxyethylene and certain polymers including, but not limited to, alginate polymers.

The polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of about 200,000 to about 7,000,000. In one embodiment the molecular weight will be from about 600,000 to about 2,000,000 and in another embodiment from about 800,000 to about 1,000,000. Polyox® is the trade name for the high molecular weight polyoxyethylene produced by Union Carbide.

The polyoxyethylene may be present in an amount from about 1% to 90%, in one embodiment from about 5% to 50% and in another embodiment from about 10% to 20% by weight of the oral care carrier component of the oral care compositions of the present invention. The dosage of foaming agent in the individual strip or tape (i.e., a single dose) is about 0.01 to 0.9% by weight, 0.05 to 0.5% by weight, and in another embodiment about 0.1 to 0.2% by weight.

Another agent optionally included in the oral care tape or strips of the invention is a surfactant or a mixture of compatible surfactants. Suitable surfactants are those which are reasonably stable throughout a wide pH range, for example, anionic, cationic, nonionic or zwitterionic surfactants.

Suitable surfactants are described more fully, for example, in U.S. Pat. No. 3,959,458, to Agricola et al., U.S. Pat. No. 3,937,807, to Haefele: and U.S. Pat. No. 4,051,234, to Gieske et al., which are incorporated herein by reference.

In certain embodiments, the anionic surfactants useful herein include the water-soluble salts of alkyl sulfates having from 10 to 18 carbon atoms in the alkyl radical and the water-soluble salts of sulfonated monoglycerides of fatty acids having from 10 to 18 carbon atoms. Sodium lauryl sulfate, sodium lauroyl sarcosinate and sodium coconut monoglyceride sulfonates are examples of anionic surfactants of this type. Mixtures of anionic surfactants may also be utilized.

In another embodiment, cationic surfactants useful in the present invention can be broadly defined as derivatives of aliphatic quaternary ammonium compounds having one long alkyl chain containing from about 8 to 18 carbon atoms such as lauryl trimethylammonium chloride, cetyl pyridinium chloride, cetyl trimethylammonium bromide, di-isobutylphenoxyethyldimethylbenzylammonium chloride, coconut alkyltrimethylammonium nitrite, cetyl pyridinium fluoride, and mixtures thereof.

Illustrative cationic surfactants are the quaternary ammonium fluorides described in U.S. Pat. No. 3,535,421 to Briner et al., herein incorporated by reference. Certain cationic surfactants can also act as germicides in the compositions.

Illustrative nonionic surfactants that can be used in the compositions of the invention can be broadly defined as compounds produced by the condensation of alkylene oxide groups (hydrophilic in nature) with an organic hydrophobic compound which may be aliphatic or alkylaromatic in nature. Examples of suitable nonionic surfactants include, but are not limited to, the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

In certain embodiments, zwitterionic synthetic surfactants useful in the present invention can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate or phosphonate. Illustrative examples of the surfactants suited for inclusion into the composition include, but are not limited to, sodium alkyl sulfate, sodium lauroyl sarcosinate, cocoamidopropyl betaine and polysorbate 20, and combinations thereof.

The surfactant or mixtures of compatible surfactants can be present in the compositions of the present invention from about 0.1% to about 5.0%. in another embodiment from about 0.3% to about 3.0% and in another embodiment from about 0.5% to about 2.0% by weight of the total composition. The dosage of surfactant in the individual strip or tape (i.e., a single dose) is about 0.001 to 0.05% by weight, 0.003 to 0.03% by weight, and in another embodiment about 0.005 to 0.02% by weight.

The oral care strips or tape compositions of the invention may also include a flavoring agent. Flavoring agents which are used in the practice of the present invention include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint.

The flavoring agent is incorporated in the oral composition at a concentration of about 0.1 to about 5% by weight and about 0.5 to about 1.5% by weight. The dosage of flavoring agent in the individual strip or tape (i.e., a single dose) is about 0.001 to 0.05% by weight and in another embodiment about 0.005 to 0.015% by weight.

The oral care strips or tape compositions of the invention may also include one or more adhesive agents to aid the tape or strip to adhere to the tissues of the oral cavity. Suitable adhesives include, but are not limited to, both polymers with limited water solubility as well as polymers lacking water solubility. These polymers deposit a thin film on both the oral cavity's soft and hard tissues when saliva combines with the instant composition. Suitable limited water solubility adhesives include, but are not limited to, hydroxy ethyl or propyl cellulose. Adhesives lacking water solubility and suitable for the compositions of the invention include, but are not limited to, ethyl cellulose, polyox resins and silicones. Adhesives lacking water solubility are incorporated into the instant invention by using a small amount of ethyl alcohol or another alcohol safe for use in the oral cavity and the human body.

Another possible adhesive suitable for use in the instant composition is polyvinylpyrrolidone ("PVP") with a molecular weight of about 50,000 to about 300,000, a suitable PVP is available from GAF Chemicals Corporation.

Still another possible adhesive suitable for use in the instant composition is a combination of Gantrez and the semi-synthetic, water-soluble polymer carboxymethyl cellulose ("CMC"). Certain embodiments encompass a mixture of 2:1 to 1:1 (Gantrez to CMC). Suitable for use in the combination is Gantrez with a M.W. of about 30,000 to about 1,000,000 available from GAF Chemicals Corporation and CMC with a M.W. of about 90,000 to about 700,000 available from Aqualon Company.

The oral care strips or tape compositions of the invention also may optionally include one or more chelating agents able to complex calcium found in the cell walls of the bacteria. Binding of this calcium weakens the bacterial cell wall and augments bacterial lysis.

Another group of agents suitable for use as chelating agents in the present invention are the soluble pyrophosphates. The pyrophosphate salts used in the present compositions can be any of the alkali metal pyrophosphate salts. In certain embodiments, salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition is generally enough to provide at least 1.0% pyrophosphate ions, from about 1.5% to about 6%, from about 3.5% to about 6% of such ions. The dosage chelating agent in the individual strip or tape (i.e., a single dose) is about 0.01 to 0.6% by weight and in another embodiment about 0.035 to 0.06% by weight.

The oral care strips or tape compositions of the invention also optionally include one or more polymers. Such materials are well known in the art, being employed in the form of their free acids or partially or fully neutralized water soluble alkali metal (e.g. potassium and sodium) or ammonium salts. Certain embodiments include 1:4 to 4:1 copolymers of maleic anhydride or acid with another polymerizable ethylenically unsaturated monomer, for example, methyl vinyl ether(methoxyethylene) having a molecular weight (M.W.) of about 30,000 to about 1,000,000. These copolymers are available for example as Gantrez AN 139 (M.W. 500,000), AN 119 (M.W. 250,000) and S-97 Pharmaceutical Grade (M.W. 70,000), of GAF Chemicals Corporation.

Other operative polymers include those such as the 1:1 copolymers of maleic anhydride with ethyl acrylate, hydroxyethyl methacrylate. N-vinyl-2-pyrrolidone, or ethylene, the latter being available for example as Monsanto EMA No. 1103. M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate mid the like. Copolymers contain sufficient carboxylic salt groups for water-solubility.

A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight from 1,000-2,000,000, described in U.S. Pat. No. 4,842,847. Jun. 27, 1989 to Zahid, incorporated herein by reference.

Another useful class of polymeric agents includes polyamino acids, particularly those containing proportions of anionic surface-active amino acids such as aspattic acid, glutamic acid and phosphoserine, as disclosed in U.S. Pat. No. 4,866,161 Sikes et al., incorporated herein by reference.

The oral care strips or tape compositions of the invention may also optionally include one or more enzymes. Useful enzymes include any of the available proteases, glucanohydrolases, endoglycosidases, amylases, mutanases, lipases and mucinases or compatible mixtures thereof. In certain embodiments, the enzyme is a protease, dextranase, endoglycosidase and mutanase. In another embodiment, the enzyme is papain, endoglycosidase or a mixture of dextranase and mutanase. Additional enzymes suitable for use in the present invention are disclosed in U.S. Pat. No. 5,000,939 to Dring et al., U.S. Pat. No. 4,992,420; U.S. Pat. No. 4,355,022; U.S. Pat. No. 4,154,815; U.S. Pat. No. 4,058,595; U.S. Pat. No. 3,991,177; and U.S. Pat. No. 3,696,191 all incorporated herein by reference. An enzyme of a mixture of several compatible enzymes in the current invention constitutes from about 0.002% to about 2.0% in one embodiment or from about 0.05% to about 1.5% in another embodiment or in yet another embodiment from about 0.1% to about 0.5%.

Water may also be present in the oral compositions of the invention. Water, employed in the preparation of commercial oral compositions should be deionized and free of organic impurities. Water commonly makes up the balance of the compositions and includes from about 10% to 50%, about 20% to 40% or about 10% to 15% by weight of the oral compositions. This amount of water includes the free water which is added plus that amount which is introduced with other materials such as with sorbitol or any components of the invention.

In preparing oral care strips or tape compositions, it is sometimes necessary to add some thickening material to provide a desirable consistency. In certain embodiments, the thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate or finely divided silica can be used as component of the thickening composition to further improve the composition's texture. Thickening agents in an amount from 0.5% to 5.0% by weight of the total composition can be used.

Within certain embodiments of the oral compositions, it is also desirable to incorporate a humectant to prevent the composition from hardening upon exposure to air. Certain humectants can also impart desirable sweetness or flavor to dentifrice compositions. The humectant, on a pure humectant basis, generally includes from about 15% to 70% in one embodiment or from about 30% to 65% in another embodiment by weight of the dentifrice composition.

Suitable humectants include edible polyhydric alcohols such as glycerine, sorbitol, xylitol, propylene glycol as well as other polyols and mixtures of these humectants. Mixtures of glycerine and sorbitol may be used in certain embodiments as the humectant component of the toothpaste compositions herein.

In addition to the above described components, the embodiments of this invention can contain a variety of optional dentifrice ingredients some of which are described below. Optional ingredients include, for example, but are not limited to, adhesives, sudsing agents, flavoring agents, sweetening agents, additional antiplaque agents, abrasives, and coloring agents. These and other optional components are further described in U.S. Pat. No. 5,004,597, to Majeti; U.S. Pat. No. 3,959,458 to Agricola et al. and U.S. Pat. No. 3,937,807, to Haefele, all being incorporated herein by reference.

The compositions of the present invention can be made using methods which are common in the oral product area.

In one illustrative embodiment, the toothtape is made by dissolving acrylate copolymers and PVP In ethanol and mixing for 2 minutes at 2600 rpm to form Premix 1.

Actives such as, for example, vitamins, CPC, fluoride, abrasives, and any other desired active ingredients are added to Premix 1 and mixed for 2 minutes at 2600 rpm to form Premix 2.

A toothpaste base is added to Premix 2 and mixed for 2 minutes at 3000 rpm. The final slurry is cast on hydrophobic surface with approximately 0.2 mm wet thickness. Film is dried in air-circulating oven at about 175-180° C. for 1-2 hr.

The present invention in its method aspect involves applying to the oral cavity a safe and effective amount of the compositions described herein. These amounts, for example, from about 20 mm$^2$ to 2000 mm$^2$ of the strip or tape, is kept in the mouth from about 15 seconds to about 12 hours. In addition, the oral care strip or tape can be left alone to clean the teeth or can be used with a brush.

The following examples further describe and demonstrate illustrative embodiments within the scope of the present invention. The examples are given solely for illustration and are not to be construed as limitations of this invention as many variations are possible without departing from the spirit and scope thereof.

EXAMPLES

Example 1

Example 1 illustrates illustrative embodiments of the compositions for "Toothtape" for the dentifrice and for a single dosage. In certain embodiments, the single dosage may be a precut or a perforated strip to allow the user to easily use a strip with a predetermined dosage. In other embodiments, the strips are not precut and the user can tear or cut the strip in a desired length.

TABLE 1

| Ingredient | % in dentifrice | wt./1 g dentifrice or 1 dose toothtape |
|---|---|---|
| Abrasive | 10.00 | 0.100 |
| Flavor | 0.30 | 0.003 |
| SLS | 0.50 | 0.005 |
| Saccharin | 0.30 | 0.003 |
| Sorbitol (70%) | 10.00 | 0.100 |
| Alginate Polymer | 20-78.9 | 0.2-0.789 |
| Water | Balance | Balance |

The toothtape dose has an approximate surface area: of about 200 mm$^2$ (40 mm×5 mm when applied to upper front teeth.

Example 2

Example 2 illustrates various illustrative embodiments of the toothtape and Table 1 illustrates the sensory perception of the embodiments based oil the average of 5 panelists.

TABLE 2

|  | Formula A | Formula B | Formula C | Formula D | Formula E | Formula F |
|---|---|---|---|---|---|---|
| Abrasive | 10.00 | 10.00 | 10.00 | 10.00 | 20.00 | 15.00 |
| Flavor | 0.40 | 0.00 | 0.30 | 0.30 | 0.00 | 0.40 |
| SLS | 0.50 | 0.50 | 0.50 | 0.50 | 0.40 | 0.40 |
| Saccharin | 0.20 | 0.00 | 0.30 | 0.30 | 0.40 | 0.10 |
| Sorbitol | 0.00 | 0.00 | 0.00 | 0.00 | 0.00 | 0.00 |
| Alginate Polymer | 20.00 | 20.00 | 30.00 | 30.00 | 40.00 | 40.00 |
| Water | Balance | Balance | Balance | Balance | Balance | Balance |

TABLE 3

| Sample | Structure | Adhesion | Dissolution | Amount of foam | Residue | Level of flavor | Bitterness | Comments Avg. of 5 panelists |
|---|---|---|---|---|---|---|---|---|
| Formula A | 3.25 | 3.75 | 4.25 | 4.25 | 4.0 | 2.25 | 3.0 | best flavor |
| Formula B | 3.0 | 3.75 | 3.0 | 4.5 | 2.6 | 1.0 | 2.25 | worse taste |
| Formula C | 3.75 | 3.5 | 3.75 | 4.5 | 4.3 | 1.5 | 3.25 | No flavor |
| Formula D | 3.75 | 3.25 | 3.9 | 4.5 | 3.75 | 1.75 | 3.0 | No flavor |
| Formula E | 2.8 | 1.6 | 2.9 | 4.0 | 4.2 | 3.4 | 4.5 | sweet, no flavor, little bitter |
| Formula F | 2.3 | 2.5 | 2.9 | 4 | 4.2 | 1.5 | 2.8 | very sweet, no flavor, very bitter |

Keys:

Structure: Brittle = 1, Pliable = 5.

Adhesion: Poor = 1, Good = 5. Should adhere well before brushing and then remain until it dissolves with brushing.

Dissolution: Poor = 1, Good = 5. Target is 20-30 s to complete dissolution.

Amount of foam: Poor = 1, Good = 5. Target is same as a kid's dentifrice.

Residue: Lot = 1, None = 5. Target is none.

Levels of flavor: None = 1, Strong = 5.

Bitterness: Lot = 1, None = 5. Target is none.

Example 3

Example 3 illustrates various illustrative embodiments of the toothtape of the invention for immediate release.

TABLE 4

TOOTHTAPE compositions for Immediate Release of Actives

| Ingredient | Formula A % | Formula B % | Formula C % | Formula D % | Formula E % |
|---|---|---|---|---|---|
| Polyethylene glycol 600 | 1.55 | 1.56 | 3.99 | 4.49 | 3.08 |
| Sodium CMC | 0.31 | 0.31 | 0.47 | 0.44 | 0.16 |
| CP purified water | 3.64 | 3.66 | 5.51 | 5.18 | 3.08 |
| Sodium Saccharin USP | 0.155 | 0.156 | 0.23 | 0.22 | 0.13 |
| Tetrasodium Pyrophosphate | 0.26 | 0.26 | 0.12 | 0.37 | 0.22 |
| FD&Blue no. 1-1% soln | 0.083 | 0.083 | 0.125 | 0.12 | 0.07 |
| Sorbitol-non-crystalizing-NF | 31.4 | 31.53 | 50.16 | 47.43 | 26.56 |
| Synthetic glycerin | — | — | 4.73 | 6.98 | 2.96 |
| Sodium Fluoride | 0.124 | 0.125 | 0.19 | 0.18 | 0.11 |
| Abrasive silica (Zeodent 115) | 13.19 | 19.86 | 20.92 | 19.64 | 12.18 |
| Liquid Flavor | 0.37 | 0.37 | 0.56 | 0.53 | 0.31 |
| Sodium Lauryl Sulfate | 0.62 | 10.81 | 1.18 | 1.2 | 0.86 |
| Spray-dried Flavor | — | — | 0.11 | 0.4 | 0.83 |
| Acrylic copolymers | 12.78 | 13.175 | 0.85 | 1.13 | 13.25 |
| Polyvinylpyrrolidone | 3.83 | 2.14 | 0.76 | 0.54 | 3.79 |
| Vitamin E | — | — | 0.3 | 0.33 | 0.33 |
| Vitamin E-acetate | — | — | 0.04 | 0.08 | 0.13 |
| Vitamin $B_5$ | — | — | 0.03 | 0.06 | 0.07 |
| Vitamin C (ascorbyl palmitate) | — | — | 0.013 | 0.02 | 0.03 |
| Folic Acid | — | — | — | 0.03 | 0.02 |
| CPC | — | 0.1 | — | — | — |
| Triclosan | — | — | — | — | — |
| Ethanol | 31.688 | 25.861 | 9.712 | 10.63 | 31.83 |
| Total | 100 | 100 | 100 | 100 | 100 |
| Final weight (gr) | 35.47 | 77.05 | 84.26 | 91.7 | 84.5 |

Other actives can be used, including: cholorhexidine, gluconate. solbrol, enzymes such as GOX, HOX, tannase, papain; glucoamylase, hydrogen peroxide, Q10, biotin, vitamins A and D, stannous fluoride, zinc citrate, essential oils, herbals such as magnolia, rosemary, greent tea.

Example 4

Example 4 illustrates various illustrative embodiments of the toothtape of the invention for sustained release.

TABLE 5

TOOTHTAPE compositions for Sustained Release of Actives

| Ingredient | Formula A % | Formula B % | Formula C % | Formula D % | Formula E % | Formula F % |
|---|---|---|---|---|---|---|
| Polyethylene glycol 600 | 1.55 | 1.55 | 1.55 | 1.55 | 1.55 | 1.55 |
| Sodium CMC | 0.31 | 0.31 | 0.31 | 0.31 | 0.31 | 031 |
| CP purified water | 3.64 | 3.64 | 3.64 | 3.64 | 3.64 | 3.64 |
| Sodium Saccharin USP | 0.155 | 0.155 | 0.155 | 0.155 | 0.155 | 0.155 |
| tetrasodum Pyrophosphate | 0.26 | 0.26 | 0.26 | 0.26 | 0.26 | 0.26 |
| FD&Blue no. 1-1% soln | 0.083 | 0.083 | 0.083 | 0.083 | 0.083 | 0.083 |
| Sorbitol-non-crystalizing-NF (70% soln) | 31.40 | 31.40 | 31.40 | 31.40 | 31.40 | 31.40 |
| Synthetic glycerin | — | — | — | — | — | — |
| Sodium Fluoride | 0.124 | 0.124 | 0.124 | 0.124 | 0.124 | 0.124 |
| Abrasive Silica (zeodent 115) | 10.00 | 10.00 | 15.00 | 15.00 | 10.00 | 10.00 |
| Prophy | 15.50 | 15.50 | 10.50 | 10.50 | 15.50 | 15.50 |
| Liquid Flavor | 3.00 | 3.00 | 3.00 | 3.00 | — | — |
| Sodium Lauryl Sulfate | 1.20 | 1.20 | 1.20 | 1.20 | 1.20 | 1.20 |
| Spray-dried Flavor | — | — | — | — | 3.00 | 3.00 |
| Acrylic Copolymers | 12.00 | 12.00 | 12.00 | 12.00 | 12.00 | 12.00 |
| Polyvinylpyrrolidone | 3.00 | 3.00 | 3.00 | 3.00 | 3.00 | 3.00 |
| Chitosan | 5.00 | 5.00 | 5.00 | 5.00 | 5.00 | 5.00 |
| Vitamin E | 2.00 | — | 2.00 | — | 2.00 | — |
| Vitamin E-acetate | 0.20 | — | 0.20 | — | 0.20 | — |
| Vitamin $B_5$ | 0.05 | — | 0.05 | — | 0.05 | — |
| Vitamin C (ascorbyl palmitate) | 0.05 | — | 0.05 | — | 0.05 | — |
| Folic Acid | 0.05 | — | 0.05 | — | 0.05 | — |
| CPC | 0.02 | 0.02 | 0.02 | 0.02 | 0.02 | 0.02 |
| Ethanol | 10.41 | 12.76 | 10.41 | 12.76 | 10.41 | 12.76 |
| Total | 100 | 100 | 100 | 100 | 100 | 100 |

What is claimed is:

1. A method of cleaning the oral cavity of a mammal, the method comprising:
   (i) applying the dentifrice in the form of a solid tape or strip capable of adhering to the surface of the oral cavity, comprising at least one abrasive, and at least one fluoride source, wherein said dentifrice is capable of cleaning the teeth and/or oral cavity and is capable of dissolution upon brushing to a surface of the oral cavity; and
   (ii) apply agitation to the dentifrice, so as to mechanically rupture and/or facilitate dissolution of the dentifrice.

2. The method of claim 1 further comprising at least one foaming agent.

3. The method of claim 1 further comprising at least one surfactant.

4. The method of claim 1, wherein the tape or film is in precut segments.

5. The method of claim 1 further comprising at least one additional ingredient selected from the group consisting of vitamins, polymers, flavoring agents, enzymes, humectants, preservatives, and combinations thereof.

6. The method of claim 1, wherein the abrasive is chosen from the group consisting of abrasive silica, sodium metaphosphate, potassium metaphosphate, tricalcium phosphate, dihydrated dicalcium phosphate, aluminum silicate, calcined alumina, bentonite or other siliceous materials, and combinations thereof.

7. The method of claim 1, wherein the fluoride source is one member chosen from sodium fluoride, potassium fluoride, sodium fluorosilicate, sodium monfluorophosphate (MFP), ammonium fluorosilicate, stannous fluoride and stannous chloride.

8. The method of claim 2, wherein the foaming agent is sodium alginate or polyoxyethylene.

9. The method of claim 5, wherein the flavoring agent is one member chosen from oil of wintergreen, oil of peppermint, oil of spearmint, oil of sassafras, oil of clove, aspartame, acesulfame, saccharin, dextrose, levulose and sodium cyclamate and combinations thereof.

10. The method of claim 1, wherein the at least one abrasive is present in an amount of about 1 to 20 wt. %.

11. The method of claim 1, wherein the at least one fluoride source is present in an amount of about 0.01 to 5 wt. %.

12. The method of claim 2, wherein the at least one foaming agent is present in an amount of about 1 to 90 wt. %.

13. The method of claim 1 further comprising at least one flavoring agent in an amount of about 0.01 to 5 wt. %.

14. The method of claim 1 further comprising at least one humectant in an amount of about 0.01 to 5 wt. %.

* * * * *